United States Patent [19]

Stettendorf et al.

[11] Patent Number: 4,721,724

[45] Date of Patent: Jan. 26, 1988

[54] FORMULATIONS CONTAINING AZOLE DERIVATIVES, AND THEIR USE FOR ATRAUMATIC NAIL REMOVAL

[75] Inventors: Sigrid Stettendorf, Wuppertal; Karlheinz Adams, Cologne, both of Fed. Rep. of Germany

[73] Assignee: Bayer Aktiengesellschaft, Leverkusen, Fed. Rep. of Germany

[21] Appl. No.: 868,407

[22] Filed: May 29, 1986

[30] Foreign Application Priority Data

Jun. 5, 1985 [DE]  Fed. Rep. of Germany ....... 3520098

[51] Int. Cl.$^4$ .......................................... A61K 31/415
[52] U.S. Cl. .................................................... 514/396
[58] Field of Search ................................ 514/385, 396

[56] References Cited

U.S. PATENT DOCUMENTS

| | | | |
|---|---|---|---|
| 3,725,549 | 4/1973 | Buchel et al. ........................ | 514/396 |
| 4,118,487 | 10/1978 | Regel et al. ......................... | 514/396 |
| 4,323,558 | 4/1982 | Nelson ................................ | 424/164 |
| 4,457,938 | 7/1984 | von Bittera et al. ................ | 514/396 |
| 4,608,249 | 8/1986 | Otsuka et al. ....................... | 424/80 |

FOREIGN PATENT DOCUMENTS 1180661  1/1985  Canada ................................. 514/396

OTHER PUBLICATIONS

Gregory, *Uses & Applications of Chemicals*, p. 630 (1939).

*Primary Examiner*—Albert T. Meyers
*Assistant Examiner*—F. L. Krosnick
*Attorney, Agent, or Firm*—Sprung Horn Kramer & Woods

[57] ABSTRACT

A formulation for atraumatic nail removal containing 0.05–1.5 parts by weight of an azole derivative, 5–60 parts by weight of urea, 0–40 parts by weight of lipophilic wetting agent, 0–30 parts by weight of a factor conferring consistency, 0–40 parts by weight of an oil body or spreading agent, 0–0.2 parts by weight of a stabilizer and 20–60 parts by weight of vehicle.

3 Claims, No Drawings

FORMULATIONS CONTAINING AZOLE DERIVATIVES, AND THEIR USE FOR ATRAUMATIC NAIL REMOVAL

The invention relates to formulations containing azole derivatives and to their use for atraumatic nail removal.

The azole derivatives which may be particularly mentioned are bifonazole of the formula

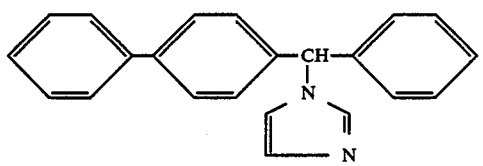

and clotrimazole of the formula

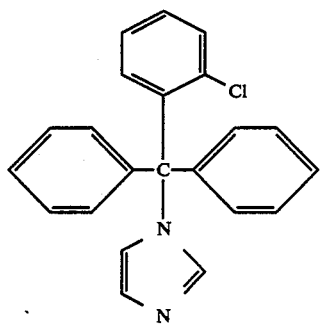

These compounds can be contained in the formulations according to the invention in amounts of 0.05–1.5, preferably 0.1–1, in particular one, part(s) by weight.

Further constituents are:
(a) Urea in amounts of 5–60, preferably 10–50, in particular 20–40, parts by weight,
(b) lipophilic wetting agents such as, for example, lanolin, wool alcohols, cholesterol, mixtures of higher molecular weight esters (Dehymuls E), in amounts of 0–40, preferably 5–30, in particular 10–20, parts by weight,
(c) factors conferring consistency, such as, for example, white beeswax, microwax, hard paraffin, spermaceti, glycerol fatty acid esters, or cetylstearyl alcohol, in amounts of 0–30 preferably 5–20, in particular 5–10, parts by weight,
(d) oil bodies or spreading agents, such as isopropyl myristate, groundnut oil, castor oil, silicone oil, paraffin, 2-octyldodecanol, decyl oleate, or triglyceride of caprylic/capric acids (Myritol 318), in amounts of 0–40, preferably 10–30, in particular 10–20, parts by weight,
(e) stabilizers such as, for example, tocopherol, butylhydroxyanisole, or butylhydroxytoluene, in amounts of 0–0.2, preferably 0.01–0.1, in particular 0.01–0.05, parts by weight,
(f) Vehicles such as, for example, soft white paraffin, mixtures of high molecular weight mixed esters of pentaerythritol fatty acid esters and citric acid fatty alcohol esters with fatty alcohol—fatty acid esters and mineral fats (Dehymuls K), and mixtures of liquid paraffin, vaseline, waxes, cholesterol, fatty alcohols and glycerol fatty acid esters (Protegin X), in amounts of 20–60, preferably 20–50, in particular 25–40, parts by weight.

The formulation according to the invention can be prepared by mixing the vehicles, lipophilic wetting agents factors conferring consistency, oil bodies or spreading agents, and stabilizers at elevated temperature, for example at 50°–80° C., and then adding the azole derivative and the urea. Urea is preferably added last.

The formulation according to the invention can be used for atraumatic nail removal in cases of onychomycoses in humans and animals.

The azole derivatives display their antimycotic action in the formulation according to the invention by an improved penetration, for the time until the nail is removed, on the nail which is infected by mycosis. Because of its hydrating and keratolytic properties, urea brings about loosening and subsequent atraumatic detachment of the infected body of the nail. The experiment which follows illustrates this.

The composition according to example 1, is applied every 24 hours to the fungus-infected nails, and is left under an occlusive dressing for 24 hours. Using this procedure it is possible, as a rule, to detach the fungus-infected nail atraumatically within a period of between 6 and 10 days.

EXAMPLE 1

| Bifonazole | 1% |
|---|---|
| Urea | 40% |
| Anhydrous lanolin | 20% |
| White beeswax | 5% |
| Soft white paraffin | 34% |
| | 100% |

EXAMPLE 2

| Bifonazole | 1.50% |
|---|---|
| Urea | 20.00% |
| Anhydrous lanolin | 20.00% |
| Microwax | 10.00% |
| Isopropyl myristate | 10.00% |
| Tocopherol | 0.05% |
| Soft white paraffin | 38.45% |
| | 100.00% |

EXAMPLE 3

| Bifonazole | 1% |
|---|---|
| Urea | 40% |
| Wool alcohols | 5% |
| Spermaceti | 5% |
| 2-octyldodecanol | 20% |
| Soft white paraffin | 29% |
| | 100% |

EXAMPLE 4

| Bifonazole | 1% |
|---|---|
| Urea | 50% |
| Spermaceti | 5% |
| Silicone oil 100 | 15% |
| Dehymuls K | 29% |
| | 100% |

EXAMPLE 5

| | |
|---|---|
| Bifonazole | 0.5% |
| Urea | 30.0% |
| Cetylstearyl alcohol | 10.0% |
| Myritol 318 | 30.0% |
| Protegin X | 29.5% |
| | 100.0% |

It will be understood that the specification and examples are illustrative but not limitative of the present invention and that other embodiments within the spirit and scope of the invention will suggest themselves to those skilled in the art.

What is claimed is:

1. A method for atraumatic nail removal comprising applying to a nail an effective amount of a formulation containing 0.05–1.5 parts by weight of an azole derivative of the formula

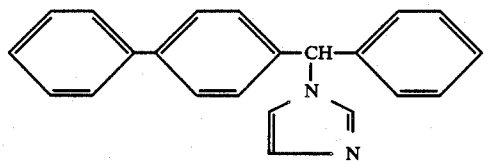

or the formula

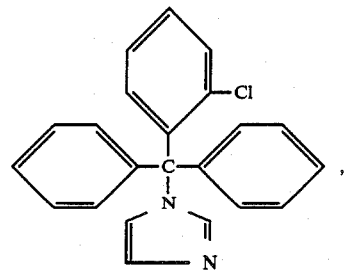

urea in the amount of 5 to 60 parts by weight, lipophilic wetting agent in an amount of 0 to 40 parts by weight, factor conferring consistency in an amount of 0 to 30 parts by weight, spreading agent in an amount of 0 to 40 parts by weight, stabilizer selected from the group consisting of tocopherol, butylhydroxyanisole and butylhydroxytoluene in an amount of 0 to 0.2 parts by weight and a pharmaceutically acceptable vehicle in an amount of 20 to 60 parts by weight and subsequently removing said nail.

2. A method according to claim 1 wherein the formulation contains urea in an amount of 10 to 50 parts by weight, lipophillic wetting agent in an amount of 5 to 30 parts by weight, factor conferring consistency in an amount of 5 to 20 parts by weight, spreading agent in an amount of 10 to 30 parts by weight, stabilizer in an amount of 0.01 to 0.1 parts by weight and vehicle in an amount of 20 to 50 parts by weight.

3. A method according to claim 1 wherein the formulation contains urea in an amount of 20 to 40 parts by weight, lipophilic wetting agent in an amount of 10 to 20 parts by weight, factor conferring consistency in an amount of 5 to 10 parts by weight, spreading agent in an amount of 10 to 20 parts by weight, stabilizer in an amount of 0.01 to 0.05 parts by weight and vehicle in an amount of 25 to 40 parts by weight.

* * * * *